United States Patent [19]

Eidenschink et al.

[11] 4,331,552
[45] May 25, 1982

[54] LIQUID CRYSTALLINE, PARTIALLY HYDROGENATED OLIGO-1,4-PHENYLENES AND DIELECTRICS AND ELECTRO-OPTICAL DISPLAY ELEMENTS CONTAINING THEM

[75] Inventors: Rudolf Eidenschink, Dieburg; Ludwig Pohl, Darmstadt; Michael Römer, Rodgau, all of Fed. Rep. of Germany; Fernando del Pino, Quito, Ecuador

[73] Assignee: Merck Patent Gesellschaft mit beschränkter Haftung, Darmstadt, Fed. Rep. of Germany

[21] Appl. No.: 213,520

[22] Filed: Dec. 5, 1980

[30] Foreign Application Priority Data

Dec. 5, 1979 [DE] Fed. Rep. of Germany ....... 2948836

[51] Int. Cl.³ ..................... G02F 1/13; C09K 3/34; C07C 13/28
[52] U.S. Cl. .................. 252/299.6; 252/299.5; 252/299.63; 350/350 R; 350/350 S; 585/20; 585/23; 585/25
[58] Field of Search ............. 252/299.5, 299.63, 299.6, 252/299.66; 350/350 R, 350 S; 585/20, 23, 25

[56] References Cited

U.S. PATENT DOCUMENTS

| | | | |
|---|---|---|---|
| 2,263,448 | 11/1941 | Smith et al. | 585/25 |
| 3,947,375 | 3/1976 | Gray et al. | 252/299 |
| 4,118,335 | 10/1978 | Krause et al. | 252/299.5 |
| 4,130,502 | 12/1978 | Eidenschink et al. | 252/299.63 |
| 4,154,697 | 5/1979 | Eidenschink et al. | 252/299.63 |
| 4,180,475 | 12/1979 | Schadt et al. | 252/299.5 |
| 4,181,625 | 1/1980 | Eidenschink et al. | 252/299.63 |
| 4,198,130 | 4/1980 | Boller et al. | 252/299.63 |
| 4,211,666 | 7/1980 | Inukai et al. | 252/299.6 |
| 4,228,029 | 10/1980 | Osman | 252/299.63 |

OTHER PUBLICATIONS

Bata, L. "Advances in Liquid Crystal Research and Applications", Proceedings of the Third Liquid Crystal Conference of the Socialist Countries, Budapest, 27-31 Aug. 1979, vol. 2, pp. 997-1002 (1981).

Scheuble, B. S., et al.; Mol. Cryst. Liq. Cryst., vol. 68, pp. 57-67, (1981).

Billard, J., et al., Mol. Cryst. Lid. Cryst., vol. 41 (Letters), pp. 217-222, (1978).

*Primary Examiner*—Teddy S. Gron
*Attorney, Agent, or Firm*—Millen & White

[57] ABSTRACT

Partially hydrogenated oligo-1,4-phenylenes of the formula

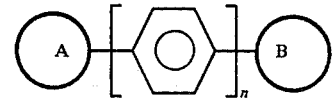

wherein n is 1 or 2, the rings A and B are identical or different and are trans-4-alkylcyclohexyl or 4-alkylcyclohex-1-enyl, and the alkyl groups in each case are of up to 10 carbon atoms, have valuable liquid crystalline properties.

9 Claims, No Drawings

LIQUID CRYSTALLINE, PARTIALLY HYDROGENATED OLIGO-1,4-PHENYLENES AND DIELECTRICS AND ELECTRO-OPTICAL DISPLAY ELEMENTS CONTAINING THEM

BACKGROUND OF THE INVENTION

For electro-optical display elements, the properties of nematic or nematic-cholesteric liquid crystal materials by which they significantly change their optical properties, such as light absorption, light scattering, double refraction, reflecting power or color, under the influence of electric fields are utilized to an increasing extent. The functioning of such display elements is based, for example, on the phenomena of dynamic scattering, the deformation of oriented phases, the Schadt-Helfrich effect in a twisted cell or the cholesteric-nematic phase transition.

Industrial application of these effects in electronic components necessitates liquid crystal dielectrics, which must fulfill a large number of requirements. Chemical stability towards moisture, air and physical influences, such as heat, radiation in the infrared, visible and ultraviolet ranges and constant and alternating electrical fields, is particuarly important in this context. A liquid crystal mesophase in the temperature range from at least +10° C. to +50° C., preferably from 0° C. to 60° C., and as low as possible a viscosity at room temperature, preferably not more than $70 \cdot 10^{-3}$ Pa.s, are also required of liquid crystal dielectrics which can be used industrially. Finally, these dielectrics must exhibit no characteristic absorption in the range of visible light, i.e., they must be colorless.

A number of liquid crystal compounds which fulfill the stability requirements demanded of dielectrics for electronic components and which also are colorless are already known. These include, in particular, the p,p-disubstituted phenyl benzoates described in German Offenlegungsschrift No. 2,139,628 and the p,p-disubstituted phenylcyclohexane derivatives described in German Offenlegungsschrift No. 2,636,684. In both these classes of compounds, and also in other known series of compounds having a liquid crystal mesophase, there are no individual compounds which form a liquid crystal nematic mesophase in the required temperature range of 10° C. to 60° C. Mixtures of two or more compounds are thus usually prepared in order to obtain substances which can be used as liquid crystal dielectrics. There are usually obtained by mixing at least one compound with a low melting point and clear point with another compound with a significantly higher melting point and clear point.

A mixture which has a melting point below that of the lower-melting component, and a clear point between the clear points of the components, is usually obtained by this procedure. However, optimum dielectrics cannot be prepared easily in this manner, since the components with the high melting points and high clear points frequently also impart a high viscosity to the mixtures. The switching times of the electro-optical display elements produced with these mixtures are thus undesirably lengthened.

SUMMARY OF THE INVENTION

Accordingly, it is an object of this invention to provide liquid crystal dielectrics which have a nematic phase in the required temperature range and which permit sufficiently short switching times in liquid crystal cells at room temperature.

It is a further object of this invention to provide such dielectrics such that, for all the types of display elements mentioned above, the important characteristic that the contrast/voltage curve be as steep as possible in the region of the threshold voltage be satisfied, i.e., that slightly exceeding the threshold voltage immediately activates the display to as full a contrast as possible.

It is another object of this invention that the threshold voltage itself be as independent of the temperature as possible, so that, in particular, the threshold voltages necessary for activation of the display at low temperatures will not be substantially higher than that which is necessary, for example, at room temperature.

Upon further study of the specification and appended claims, further objects and advantages of this invention will become apparent to those skilled in the art.

These objects have been attained in one aspect by providing the partially hydrogenated oligo-1,4-phenylenes of formula (I)

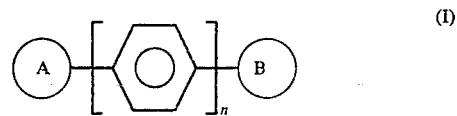

(I)

wherein n is 1 or 2 and the rings A and B, which can be identical or different, are trans-4-alkylcyclohexyl or 4-alkylcyclohex-1-enyl, the alkyl groups in each case containing up to 10 carbon atoms.

These compounds are outstandingly suitable for use as components of mixtures used to prepare liquid crystal dielectrics in which the dependence of the threshold voltage on the temperature is at a low level which has hitherto been unachieved. Moreover, the compounds of formula (I) in which n is 2, in particular, have very high clear points, in most cases significantly above 200° C. They can therefore advantageously be used for broadening the temperature range of the nematic phases of liquid crystal dielectrics.

The present invention thus relates in certain aspects to the partially hydrogenated oligo-1,4-phenylenes of formula (I) and their use as components of liquid crystal dielectrics. The invention furthermore relates in other aspects to liquid crystal dielectrics containing at least one partially hydrogenated oligo-1,4-phenylene of formula (I) and to electro-optical display elements based on a liquid crystal cell containing such a liquid crystal dielectric.

The partially hydrogenated oligo-1,4-phenylenes of this invention thus include 1,4-bis-(trans-4-alkylcyclohexyl)benzenes of formula (Ia)

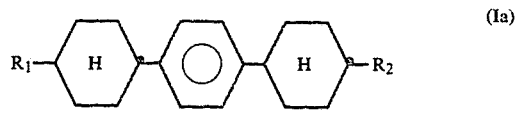

(Ia)

wherein $R_1$ and $R_2$ are identical or different and are alkyl groups of up to 10 carbon atoms; 1,4-bis-(4-alkylcyclohex-1-enyl)-benzenes of formula (Ib)

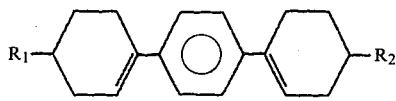

4,4'-bis-(trans-4-alkylcyclohexyl)-biphenyls of formula (Ic)

4,4'-bis-(4-alkylcyclohex-1-enyl)-biphenyls of formula (Id)

1-(trans-4-alkylcyclohexyl)-4-(4-alkylcyclohex-1-enyl)-benzenes of formula (Ie)

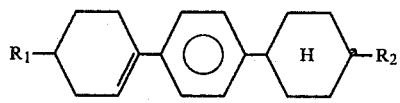

and 4-(trans-4-alkylcyclohexyl)-4'-(4-alkylcyclohex-1-enyl)biphenyls of formula (If)

wherein $R_1$ and $R_2$ in the formulae (Ib) to (If) are as defined for formula (Ia).

DETAILED DISCUSSION

When the compounds of this invention contain cyclohexane rings, these are disubstituted in the transconfiguration in the 1,4-position; in the formulae, this is expressed by the black dot on the right-hand side of the cyclohexane rings. The compounds of formulae (Ia), (Ib) and (Ie) as a rule have melting points and clear points which are lower than the analogously substituted biphenyl derivatives of the formula (Ic), (Id) and (If).

At the same time, however, they also have a considerably lower viscosity and are therefore preferably used as components which lower the viscosity of liquid crystal dielectrics, in which the remaining constituents have high clear points. In contrast, the biphenyl derivatives (Ic), (Id) and (If) have an extremely wide mesophase range, which as a rule extends over 150 Centigrade degrees and more. They are therefore preferably used for widening the mesophase range of liquid crystal dielectrics, the derivatives increasing the viscosity significantly less than other known liquid crystal compounds which have a high clear point and have hitherto been employed for this purpose. It has been found, surprisingly, that the dielectrics of this invention which contain one or more compounds of formula (I) have a particularly steep contrast/voltage curve and a very low dependence of the threshold voltage on the temperature.

The alkyl groups in the compounds of formula (I) can be straight-chain or branched, compounds with two straight-chain end group substituents being preferred. Compounds of formula (I) in which one of the radicals $R_1$ and $R_2$ is branched can occasionally be used as chiral doping substances if they are optically active as a result of the chain branching. The branched end group substituents do not contain more than one chain branching. Preferred branched end group substituents are those in which a methyl or ethyl group is in the 1- or 2-position of a longer carbon chain, for example 1-methylpropyl, 2-methylpropyl, 2-methylbutyl, 2-methyl-pentyl, 2-ethylhexyl, 1-methylheptyl or 2-methylheptyl.

In the compounds of this invention, the end group substituents $R_1$ and $R_2$ each contain up to 10 carbon atoms, i.e., 2–20 carbon atoms in total. However, preferred compounds of formula (I) are those in which $R_1$ and $R_2$ together contain 3–16 carbon atoms, in particular 4–13 carbon atoms.

The compounds of this invention can be prepared in a manner conventional for such substances.

Thus, the compounds of formula (Ia) can be obtained by a process in which a trans-(4-alkylcyclohexyl)-benzene of formula (II)

is reacted with bromine in carbon tetrachloride in the presence of iron powder to give the 4-(trans-4-alkylcyclohexyl)bromobenzene. This compound is then converted into a 1,4-bis-(trans-4-alkylcyclohexyl)-benzene (Ia) in a Grignard reaction, by reaction with magnesium in the presence of an ether, addition of a 4-alkylcyclohexanone, hydrolysis, hydrogenation and, if appropriate, cis/transisomerization and separation of the isomers.

Compounds of formula (Ie) are prepared by splitting off water by treatment with an acid, for example p-toluenesulfonic acid, instead of the hydrogenation and the subsequent steps in the abovementioned sequence for the preparation of compounds (Ia). The compounds of formula (Ib) are obtained analogously to those of formula (Ie) if a 4-(4-alkylcyclohex-1-enyl)-bromo-benzene of formula (IIa)

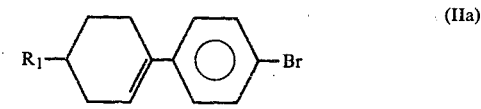

is employed as the starting material. The compounds of formula (IIa) are known from the laid-open European Patent Application No. 2136.

For the preparation of those compounds of formula (Ib) in which $R_1$ and $R_2$ are identical, it is also possible to use 1,4-dibromobenzene as the starting material, which is reacted with twice the molar amount of magnesium and then with twice the molar amount of a 4-alkylcyclohexanone. The steps of hydrolysis and splitting off of water are then carried out in the customary manner.

The biphenyl derivatives (Ic), (Id) and (If) are prepared analogously to the benzene derivatives (Ia), (Ib) and (Ie), employing 4-(trans-4-alkylcyclohexyl)-biphenyls of formula (III)

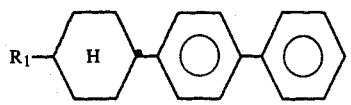

(III)

4-(4-alkylcyclohex-1-enyl)-4'-bromobiphenyls of the formula (IIIa)

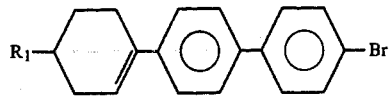

(IIIa)

and 4,4'-dibromobiphenyl, respectively, as starting materials.

These are all conventional materials. See, e.g. U.S. Pat. No. 4,154,697 for (III), from which compounds (IIIa) can be readily prepared in conventional manner.

The liquid crystal dielectrics of this invention consist of two or more components, of which at least one is a component of formula (I). Other components which are optionally used are preferably nematic or nematogenic substances from the known classes of azobenzenes, azoxybenzenes, biphenyls, Schiff's bases, in particular benzylidene derivatives, phenyl benzoates, phenylpyrimidines, phenylcyclohexanes, optionally halogenated stilbenes, diphenylacetylene derivatives, diphenyl nitrones and substituted cinnamic acids. The most important compounds which can be used as other components of this type can be characterized by formula (IV):

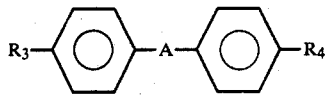

(IV)

wherein A is

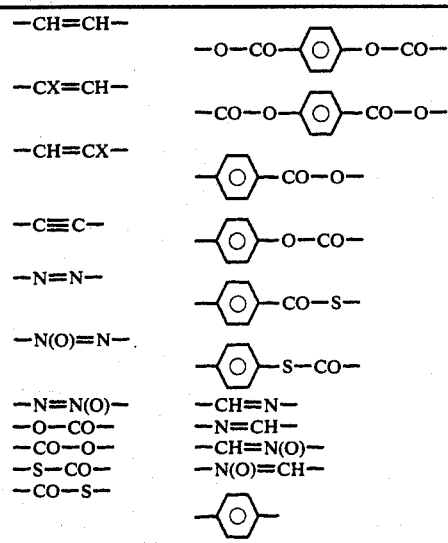

or a C-C single bond. Other possible components of the dielectrics of this invention are those compounds of formula (IV) in which one or more phenyl rings are replaced by a corresponding number of transcyclohexyl rings; it is also possible for one of these rings to be a 2,5-disubstituted pyrimidine ring.

X is halogen, preferably Cl, or —CN. $R_3$ and $R_4$ are identical or different and can be alkyl, alkoxy, alkanoyl, alkanoyloxy or alkoxycarbonyloxy radicals of up to 18, preferably up to 8, C atoms; furthermore, it is also possible for one of these radicals to be —CN, —NC, $NO_2$, $CF_3$ or halogen.

In most of these compounds, $R_3$ and $R_4$ are preferably different, one of the radicals usually being an alkyl or alkoxy group. However, a large number of other variants of the substituents envisaged are also customary. Many such substances are commercially available.

The dielectrics of this invention as a rule contain at least 30, preferably 50-99 and in particular 60-98, percent by weight of the compounds of formula (I) and (IV). Of this amount, one or more compounds of formula (I) preferably make up 3-50 percent by weight, the most preferred range being 5-25 percent by weight. The invention also comprises those liquid crystal dielectrics to which only less than 3 percent by weight, or example 0.1 to 2 percent by weight, of one or more compounds of formula (I) have been added, for example for doping purposes. On the other hand, it is also possible for up to 80 percent by weight of a dielectric of this invention to be made up of compounds of formula (I).

The dielectrics of this invention are prepared in a manner which is conventional per se. As a rule, the desired amounts of the components used in smaller amounts are dissolved in the component comprising the main constituent, preferably at elevated temperature. The completeness of the dissolving operation can be observed particularly easily if a temperature above the clear point of the main constituent is chosen.

However, it is also possible to mix solutions of the components of formulae (I) and (IV) in a suitable organic solvent, for example acetone, chloroform or methanol, and, after thorough mixing, to remove the solvent, for example, by distillation under reduced pressure. In this procedure, of course, care must be taken that no impurities or undesired doping substances are incorporated via the solvent.

The liquid crystal dielectrics of this invention can be modified by suitable additives so that they can be used in all types of liquid crystal display elements hitherto disclosed. Such additives are known to the expert and are described in detail in the relevant literature. For example, it is possible to add substances to alter the dielectric anisotropy, the viscosity, the conductivity and/or the orientation of the nematic phases. Such substances are described, for example, in German Offenlegungsschriften Nos. 2,209,127, 2,240,864, 2,321,632, 2,338,281 and 2,450,088.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

EXAMPLES

In the examples, m. denotes the melting point and c. denotes the clear point of a liquid crystal substance in degrees Centigrade; boiling points are designated by b.p. Unless otherwise indicated, data relating to parts or percentages are parts by weight or percentages by weight.

Example 1

(a) 160 g of bromine is added dropwise with stirring, to a solution of 230 g of (trans-4-n-pentylcyclohexyl)-benzene in 750 ml of carbon tetrachloride in the presence of 15 g of iron filings at a rate such that the temperature does not rise above 30°. The reaction mixture is then heated for an additional 10 minutes to the boiling point and subsequently filtered and subjected to fractional distillation. After distilling off the solvent, 163 g of 4-(trans-4-n-pentylcyclohexyl)bromobenzene is distilled off under reduced pressure; b.p. 130°–135°/0.1 mm Hg.

(b) a solution of 18 g of 4-n-pentylcyclohexanone in 30 ml of tetrahydrofuran is added dropwise, with stirring and at room temperature, to a Grignard solution prepared from 31 g of 4-(trans-4-n-pentylcyclohexyl)-bromobenzene and 3 g of magnesium filings in 100 ml of tetrahydrofuran. Hydrolysis is then carried out with a 10% aqueous solution of ammonium chloride and the organic phase is separated off, washed twice with 50 ml of water each time, dried over sodium sulfate and evaporated. The residue is dissolved in 300 ml of ethanol and the solution is hydrogenated at room temperature in the presence of 4 g of palladium-on-charcoal (5% of Pd) for 48 hours. The catalyst is then filtered off; the solvent is distilled off; the residue is taken up in 50 ml of dimethylsulfoxide; and the mixture is warmed to 100° in the absence of moisture and in the presence of 7 g of potassium tert-butylate for 16 hours. After cooling, the reaction mixture is poured into 300 ml of ice-water and the aqueous phase is extracted twice with 100 ml of methylene chloride each time. The extracts are washed with 100 ml of water, dried over calcium chloride and evaporated. The 1,4-bis-(trans-4-n-pentylcyclohexyl)-benzene which remains is recrystallized from ethanol; yield: 19 g, m. 50°, c. 196°.

The following compounds are prepared analogously:
1,4-bis-(4-trans-methylcyclohexyl)-benzene,
1-(trans-4-ethylcyclohexyl)-4-(trans-4-methylcyclohexyl)benzene,
1-(trans-4-n-propylcyclohexyl)-4-(trans-4-methylcyclohexyl)-benzene,
1-(trans-4-n-butylcyclohexyl)-4-(trans-4-methylcyclohexyl)-benzene,
1-(trans-4-n-pentylcyclohexyl)-4-(trans-4-methylcyclohexyl)-benzene,
1-(trans-4-n-hexylcyclohexyl)-4-(trans-4-methylcyclohexyl)-benzene,
1-(trans-4-n-heptylcyclohexyl)-4-(trans-4-methylcyclohexyl)-benzene,
1-(trans-4-n-octylcyclohexyl)-4-(trans-4-methylcyclohexyl)-benzene,
1-[trans-4-(2-methylbutyl)-cyclohexyl]-4-(trans-4-methylcyclohexyl)-benzene,
1,4-bis-(trans-4-ethylcyclohexyl)-benzene,
1-(trans-4-n-propylcyclohexyl)-4-(trans-4-ethylcyclohexyl)-benzene,
1-(trans-4-n-butylcyclohexyl)-4-(trans-4-ethylcyclohexyl)-benzene,
1-(trans-4-n-pentylcyclohexyl)-4-(trans-4-ethylcyclohexyl)-benzene,
1-(trans-4-n-hexylcyclohexyl)-4-(trans-4-ethylcyclohexyl)-benzene,
1-(trans-4-n-heptylcyclohexyl)-4-(trans-4-ethylcyclohexyl)-benzene,
1-(trans-4-n-octylcyclohexyl)-4-(trans-4-ethylcyclohexyl)-benzene,
1-[trans-4-(2-methylbutyl)-cyclohexyl]-4-(trans-4-ethylcyclohexyl)-benzene,
1-[trans-4-(2-ethylhexyl)-cyclohexyl]-4-(trans-4-ethylcyclohexyl)-benzene,
1,4-bis-(trans-4-n-propylcyclohexyl)-benzene, m. 77°, c. 194°,
1-(trans-4-n-butylcyclohexyl)-4-(trans-4-n-propylcyclohexyl)-benzene,
1-(trans-4-n-pentylcyclohexyl)-4-(trans-4-n-propylcyclohexyl)-benzene,
1-(trans-4-n-hexylcyclohexyl)-4-(trans-4-n-propylcyclohexyl)-benzene,
1-(trans-4-n-heptylcyclohexyl)-4-(trans-4-n-propylcyclohexyl)-benzene,
1-(trans-4-n-octycyclohexyl)-4-(trans-4-n-propylcyclohexyl)-benzene,
1-[trans-4-(2-methylbutyl)-cyclohexyl]-4-n-(trans-4-n-propyl-cyclohexyl)-benzene,
1-[trans-4-(2-ethylhexyl)-cyclohexyl]-4-(trans-4-n-propylcyclohexyl)-benzene,
1,4-bis-(trans-4-n-butylcyclohexyl)-benzene,
1-(trans-4-n-pentylcyclohexyl)-4-(trans-4-n-butylcyclohexyl)-benzene,
1-(trans-4-n-hexylcyclohexyl)-4-(trans-4-n-butylcyclohexyl)-benzene,
1-(trans-4-n-heptycyclohexyl)-4-(trans-4-n-butylcyclohexyl)-benzene,
1-(trans-4-n-octylcyclohexyl)-4-(trans-4-n-butylcyclohexyl)-benzene,
1-[trans-4-(2-methylbutyl)-cyclohexyl]-4-(trans-4-n-butylcyclohexyl)-benzene,
1-[trans-4-(2-ethylhexyl)-cyclohexyl]-4-(trans-4-n-butylcyclohexyl)-benzene,
1-(trans-4-n-hexylcyclohexyl)-4-(trans-4-n-pentylcyclohexyl)-benzene,
1-(trans-4n-heptylcyclohexyl)-4-(trans-4-n-pentylcyclohexyl)-benzene,
1-(trans-4-n-octylcyclohexyl)-4-trans-4-n-pentylcyclohexyl)-benzene,
1-[trans-4-(2-methylbutyl)-cyclohexyl]-4-(trans-4-n-pentylcyclohexyl)-benzene,
1-[trans-4-(2-ethylhexyl)-cyclohexyl]-4-(trans-4-n-pentylcyclohexyl)-benzene,
1,4-bis-(trans-4-n-hexylcyclohexyl)-benzene,
1-(trans-4-n-heptylcyclohexyl)-4-(trans-4-n-hexylcyclohexyl)-benzene,
1-(trans-4-n-octylcyclohexyl)-4-(trans-4-n-hexylcyclohexyl)-benzene,
1-[trans-4-(2-methylbutyl)-cyclohexyl]-4-(trans-4-n-hexylcyclohexyl)-benzene,
1-[trans-4-(2-ethylhexyl)-cyclohexyl]-4-(trans-4-hexylcyclohexyl)-benzene,
1,4-bis-(trans-4-n-heptylcyclohexyl)-benzene,
1-[trans-4-(2-methylbutyl)-cyclohexyl]-4-(trans-4-n-heptylcyclohexyl)-benzene and
1-[trans-4-(2-methylbutyl)-cyclohexyl]-4-(trans-4-n-octylcyclohexyl)-benzene.

Example 2

(a) 4-(Trans-4-n-pentylcyclohexyl)-biphenyl is brominated in a manner analogous to that of Example 1 (a); after distilling off the carbon tetrachloride; however, the 4-(trans-4-n-pentylcyclohexyl)-4′-bromobiphenyl which remains as a crystalline mass is recrystallized from ethanol; m. 148°, c. 185°.

(b) A grignard solution prepared from 38.5 g of 4-(trans-4-n-pentycyclohexyl)-4′-bromobiphenyl and 3 g of magnesium in 200 ml of tetrahydrofuran is reacted with 4-methylcyclohexanone in a manner analogous to that of Example 1 (b). After hydrolysis, hydrogenation and isomerization in the manner described in Example 1 (b), and after recrystallization of the product from ethanol, 4-(trans-4-n-pentylcyclohexyl)-4′-(trans-4-methylcyclohexyl)-biphenyl is obtained; m. 96°, c. 284°.

The following compounds are prepared analogously:
4,4′-bis-(trans-4-methylcyclohexyl)-biphenyl,
4-(trans-4-ethylcyclohexyl)-4′-(trans-4-methylcyclohexyl)biphenyl,
4-(trans-4-n-propylcyclohexyl)-4′-(trans-4-methylcyclohexyl)-biphenyl,
4-(trans-4-n-butylcyclohexyl)-4′-(trans-4-methylcyclohexyl)-biphenyl,
4-(trans-4-n-hexylcyclohexyl)-4′-(trans-4-methylcyclohexyl)-biphenyl,
4-(trans-4-n-heptylcyclohexyl)-4′-(trans-4-methylcyclohexyl)-biphenyl,
4-(trans-4-n-octylcyclohexyl)-4′-(trans-4-methylcyclohexyl)-biphenyl,
4-[trans-4-(2-methylbutyl)-cyclohexyl]-4′-(trans-4-methylcyclohexyl)-biphenyl,
4-[trans-4-(2-ethylhexyl)-cyclohexyl]-4′-(trans-4-methylcyclohexyl)-biphenyl,
4,4′-bis-(trans-4-ethylcyclohexyl)-biphenyl,
4-(trans-4-n-propylcyclohexyl)-4′-(trans-4-ethylcyclohexyl)-biphenyl,
4-(trans-4-n-butylcyclohexyl)-4′-(trans-4-ethylcyclohexyl)-biphenyl,
4-(trans-4-n-pentylcyclohexyl)-4′-(trans-4-ethylcyclohexyl)-biphenyl,
4-(trans-4-n-hexylcyclohexyl)-4′-(trans-4-ethylcyclohexyl)-biphenyl,
4-(trans-4-n-heptylcyclohexyl)-4′-(trans-4-ethylcyclohexyl)-biphenyl,
4-(trans-4-n-octylcyclohexyl)-4′-(trans-4-ethylcyclohexyl)-biphenyl,
4[trans-4-(2-methylbutyl)-cyclohexyl]-4′-(trans-4-ethylcyclohexyl)-biphenyl,
4-[trans-4-(2-ethylhexyl)-cyclohexyl]-4′-(trans-4-ethylcyclohexyl)-biphenyl,
4,4′-bis-(trans-4-n-propylcyclohexyl)-biphenyl, m. 63°, c. 308°,
4-(trans-4-n-butylcyclohexyl)-4′-(trans-4-n-propylcyclohexyl)-biphenyl,
4-(trans-4-n-pentylcyclohexyl)-4′-trans-4-n-propylcyclohexyl)-biphenyl,
4-(trans-4-n-hexylcyclohexyl)-4′-(trans-4-n-propylcyclohexyl)-biphenyl,
4-(trans-4-n-heptylcyclohexyl)-4′-(trans-4-n-propylcyclohexyl)-biphenyl,
4-(trans-4-n-octylcyclohexyl)-4′-(trans-4-n-propylcyclohexyl)-biphenyl,
4-[trans-4-(2-methylbutyl)-cyclohexyl]-4′-(trans-4-n-propylcyclohexyl)-biphenyl,
4-[trans-4-(2-ethylhexyl)-cyclohexyl]-4′-(trans-4-n-propylcyclohexyl)-biphenyl,
4,4′-bis-(trans-4-n-butylcyclohexyl)-biphenyl,
4-(trans-4-n-pentylcyclohexyl)-4′-(trans-4-n-butylcyclohexyl)-biphenyl,
4-(trans-4-n-hexylcyclohexyl)-4′-(trans-4-n-butylcyclohexyl)-biphenyl,
4-(trans-4-n-heptylcyclohexyl)-4′-(trans-4-n-butylcyclohexyl)-biphenyl,
4-(trans-4-n-octylcyclohexyl)-4′-(trans-4-n-butylcyclohexyl)-biphenyl,
4-[trans-4-(2-methylbutyl)-cyclohexyl]-4′-(trans-4-n-butylcyclohexyl)-biphenyl,
4-[trans-4-(2-ethylhexyl)-cyclohexyl]-4′-(trans-4-n-butylcyclohexyl)-biphenyl,
4,4′-bis-(trans-4-n-pentylcyclohexyl)-biphenyl, m. 43°, c. 300°,
4-(trans-4-n-hexylcyclohexyl)-4′-(trans-4-n-pentylcyclohexyl)-biphenyl, m. 84°, c. 240°,
4-(trans-4-n-heptylcyclohexyl)-4′-(trans-4-n-pentylcyclohexyl)-biphenyl,
4-(trans-4-n-octylcyclohexyl)-4′-(trans-4-n-pentylcyclohexyl)-biphenyl,
4-[trans-4-(2-methylbutyl)-cyclohexyl]-4′-(trans-4-n-pentylcyclohexyl)-biphenyl,
4-[trans-4-(2-ethylhexyl)-cyclohexyl]-4′-(trans-4-n-pentylcyclohexyl)-biphenyl,
4,4′-bis-(trans-4-n-hexylcyclohexyl)-biphenyl,
4-(trans-4-n-heptylcyclohexyl)-4′-(trans-4-n-hexylcyclohexyl)-biphenyl,
4-(trans-4-n-octylcyclohexyl)-4′-(trans-4-n-hexylcyclohexyl)-biphenyl,
4-[trans-4-(2-methylbutyl)-cyclohexyl]-4′-(trans-4-n-hexylcyclohexyl)-biphenyl,
4-[trans-4-(2-ethylhexyl)-cyclohexyl]-4′-(trans-4-n-hexylcyclohexyl)-biphenyl,
4,4′-bis-(trans-4-n-heptylcyclohexyl)-biphenyl,
4-[trans-4-(2-methylbutyl)-cyclohexyl]-4′-(trans-4-n-heptylcyclohexyl)-biphenyl and
4-[trans-4-(2-methylbutyl)-cyclohexyl]-4′-(trans-4-n-octylcyclohexyl)-biphenyl.

Example 3

A solution of 24 g of 1,4-dibromobenzene in 30 ml of tetrahydrofuran is slowly added dropwise to 48 g of magnesium filings in 50 ml of tetrahydrofuran while stirring. The reaction mixture is then heated to the boiling point for 2 hours and, after cooling, a solution of 28 g of 4-n-propylcyclo- hexanone in 40 ml of tetrahydrofuran is added dropwise. The mixture is subsequently stirred for a further 2 hours at 60° and hydrolysis is then carried out by dropwise addition of 1 liter of 5% aqueous hydrochloric acid. The hydrolyzed reaction mixture is extracted three times with a total of 600 ml of diethyl ether and the extracts are washed with water and evaporated, under reduced pressure in the final stages. The syrupy residue is taken up in 90 ml of acetone, 5 g of p-toluene-sulfonic acid is added and the mixture is heated to the boiling point under reflux for 4 hours. The reaction mixture is then cooled to −5° and the 1,4-bis-(4-n-propylcyclohex-1-enyl)-benzene which has crystallized out is filtered off and recrystallized from isopropyl alcohol; yield: 17.6 g, m. 75°, c. 163°.

The following compounds are prepared analogously:
1,4-bis-(4-methylcyclohex-1-enyl)-benzene,
1,4-bis-(4-ethylcyclohex-1-enyl)-benzene,
1,4-bis-(4-n-butylcyclohex-1-enyl)-benzene,
1,4-bis-(4-n-pentylcyclohex-1-enyl)-benzene,
1,4-bis-(4-n-hexylcyclohex-1-enyl)-benzene,
1,4-bis-(4-n-heptylcyclohex-1-enyl)-benzene and 1,4-bis-(4-n-octylcyclohex-1-enyl)-benzene.

If equivalent amounts of 4,4'-dibromobiphenyl are used instead of 1,4-dibromobenzene, the following compounds are prepared:
4,4'-bis-(4-methylcyclohex-1-enyl)-biphenyl,
4,4'-bis-(4-ethylcyclohex-1-enyl)-biphenyl,
4,4'-bis-(4-n-propylcyclohex-1-enyl)-biphenyl,
4,4'-bis-(4-n-butylcyclohex-1-enyl)-biphenyl,
4,4'-bis-(4-n-pentylcyclohex-1-enyl)-biphenyl,
4,4'-bis-(4-n-hexylcyclohex-1-enyl)-biphenyl and
4,4'-bis-(4-n-heptylcyclohex-1-enyl)-biphenyl.

Example 4

A solution of 31 g of 4-(4-n-pentylcyclohex-1-enyl)-bromobenzene in 50 ml of tetrahydrofuran is slowly added dropwise to 24 g of magnesium filings in 50 ml of tetrahydrofuran, while stirring. The reaction mixture is then heated to the boiling point for 2 hours and, after cooling, a solution of 14 g of 4-n-propylcyclohexanone in 20 ml of tetrahydrofuran is added dropwise. The mixture is subsequently stirred for a further 2 hours at 60° and hydrolysis is then carried out by dropwise addition of 500 ml of 5% aqueous hydrochloric acid. The hydrolyzed reaction mixture is extracted four times with a total of 800 ml of diethyl ether and the extracts are washed with water and evaporated, under reduced pressure in the final stages. The syrupy residue is dissolved in 90 ml of acetone and this solution is heated to the boiling point under reflux with 5 g of p-toluenesulfonic acid for 4 hours. The reaction mixture is then cooled to −5° and the 1-(4-n-pentylcyclohex-1-enyl)-4-(4-n-propylcyclohex-1-enyl)-benzene which has crystallized out is filtered off and recrystallized from isopropyl alcohol; yield: 23.6 g of colorless crystals, m. 35°, c. 141°.

The following compounds are prepared analogously:
1-(4-ethylcyclohex-1-enyl)-4-(4-methylcyclohex-1-enyl)-benzene,
1-(4-n-propylcyclohex-1-enyl)-4-(4-methylcyclohex-1-enyl)-benzene,
1-(4-n-butylcyclohex-1enyl)-4-(4-methylcyclohex-1-enyl)-benzene,
1-(4-n-pentylcyclohex-1enyl)-4-(4-methylcyclohex-1-enyl)-benzene,
1-(4-n-hexylcyclohex-1-enyl)-4-(4-methylcyclohex-1-enyl)-benzene,
1-(4-n-heptylcyclohex-1-enyl)-4-(4-methylcyclohex-1-enyl)-benzene,
1-(4-n-octylcyclohex-1-enyl)-4-(4-methylcyclohex-1-enyl)benzene,
1-(4-n-nonylcyclohex-1-enyl)-4-(4-methylcyclohex-1-enyl)-benzene,
1-(4-n-decylcyclohex-1-enyl)-4-(4-methylcyclohex-1-enyl)-benzene,
1-[4-(2-methylbutyl)-cyclohex-1-enyl]-4-(4-methylcyclohex-1-enyl)-benzene,
1-(4-n-propylcyclohex-1-enyl)-4-(4-ethylcyclohex-1-enyl)-benzene,
1-(4-n-butylcyclohex-1-enyl)-4-(4-ethylcyclohex-1-enyl)-benzene,
1-(4-n-pentylcyclohex-1-enyl)-4-(4-ethylcyclohex-1-enyl)-benzene,
1-(4-n-hexylcyclohex-1-enyl)-4-(4-ethylcyclohex-1-enyl)-benzene,
1-(4-n-heptylcyclohex-1-enyl)-4-(4-ethylcyclohex-1-enyl)-benzene,
1-(4-n-octylcyclohex-1-enyl)-4-(4-ethylcyclohex-1-enyl)-benzene,
1-(4-n-nonylcyclohex-1-enyl)-4-(4-ethylcyclohex-1-enyl)-benzene,
1-(4-n-decylcyclohex-1-enyl)-4-(4-ethylcyclohex-1-enyl)-benzene,
1-[4-(2-methylbutyl)-cyclohex-1-enyl]-4-(4-ethylcyclohex-1-enyl)-benzene,
1-(4-n-butylcyclohex-1-enyl)-4-(4-propylcyclohex-1-enyl)-benzene,
1-(4-n-hexylcyclohex-1-enyl)-4-(4-propylcyclohex-1-enyl)-benzene,
1-(4-n-heptylcyclohex-1-enyl)-4-(4-propylcyclohex-1-enyl)-benzene,
1-(4-n-octylcyclohex-1-enyl)-4-(4-propylcyclohex-1-enyl)-benzene,
1-(4-n-nonylcyclohex-1-enyl)-4-(4-propylcyclohex-1-enyl)-benzene,
1-(4-n-decylcyclohex-1-enyl)-4-(4-propylcyclohex-1-enyl)-benzene,
1-[4-(2-methylbutyl)-cyclohex-1-enyl]-4-(4-propylcyclohex-1-enyl)-benzene,
1-(4-n-pentylcyclohex-1-enyl)-4-(4-n-butylcyclohex-1-enyl)-benzene,
1-(4-n-hexylcyclohex-1-enyl)-4-(4-n-butylcyclohex-1enyl)-benzene,
1-(4-n-heptylcyclohex-1-enyl)-4-(4-n-butylcyclohex-1-enyl)-benzene,
1-(4-n-octylcyclohex-1-enyl)-4-(4-n-butylcyclohex-1-enyl)-benzene,
1-(4-n-nonylcyclohex-1-enyl)-4-(4-n-butylcyclohex-1-enyl)-benzene,
1-(4-n-decylcyclohex-1-enyl)-4-(4-n-butylcyclohex-1-enyl)-benzene,
1-[4-(2-methylbutyl)-cyclohex-1-enyl]-4-(4-n-butylcyclohex-1-enyl)-benzene,
1-(4-n-hexylcyclohex-1-enyl)-4-(4-n-pentylcyclohex-1-enyl)-benzene,
1-(4-n-heptylcyclohex-1-enyl)-4-(4-n-pentylcyclohex-1-enyl)-benzene,
1-(4-n-octylcyclohex-1-enyl)-4-(4-n-pentylcyclohex-1-enyl)-benzene,
1-(4-n-nonylcyclohex-1-enyl)-4-(4-n-pentylcyclohex-1-enyl)-benzene,
1-(4-n-decylcyclohex-1-enyl)-4-(4-n-pentycyclohex-1-enyl)-benzene,
1-[4-(2-methylbutyl)-cyclohex-1-enyl]-4-(4-n-pentylcyclohex-1-enyl)-benzene,
1-(4-n-heptylcyclohex-1-enyl)-4-(4-n-hexylcyclohex-1-enyl)-benzene,
1-(4-n-octylcyclohex-1-enyl)-4-(4-n-hexylcyclohex-1-enyl)-benzene,
1-(4-n-nonylcyclohex-1-enyl)-4-(4-n-hexylcyclohex-1-enyl)-benzene,
1-(4-n-decylcyclohex-1-enyl)-4-(4-n-hexylcyclohex-1-enyl)-benzene,
1-[4-(2-methylbutyl)-cyclohex-1-enyl]-4-(4-n-hexylcyclohex-1-enyl)-benzene,
4-(4-ethylcyclohex-1-enyl)-4'-(4-methylcyclohex-1-enyl)-biphenyl,
4-(4-n-propylcyclohex-1-enyl)-4'-(4-methylcyclohex-1-enyl)-biphenyl,
4-(4-n-butylcyclohex-1-enyl)-4'-(4-methylcyclohex-1-enyl)-biphenyl,
4-(4-n-pentylcyclohex-1-enyl)-4'-(4-methylcyclohex-1-enyl)-biphenyl,
4-(4-n-hexylcyclohex-1-enyl)-4'-(4-methylcyclohex-1-enyl)-biphenyl,
4-(4-n-heptylcyclohex-1-enyl)-4'-(4-methylcyclohex-1-enyl)-biphenyl, 4-(4-n-octylcyclohex-1-enyl)-4'-(4-methylcyclohex-1-enyl)-biphenyl,
4-(4-n-nonylcyclohex-1-enyl)-4'-(4-methylcyclohex-1-enyl)-biphenyl,
4-(4-n-decylcyclohex-1-enyl)-4'-(4-methylcyclohex-1-enyl)-biphenyl,
4-[4-(2-methylbutyl)-cyclohex-1-enyl]4'-(4-methylcyclohex-1-enyl)-biphenyl,
4-(4-n-propylcyclohex-1-enyl)-4'-(4-ethylcyclohex-1-enyl)-biphenyl,
4-(4-n-butylcyclohex-1-enyl)-4'-(4-ethylcyclohex-1-enyl)-biphenyl,
4-(4-n-pentylcyclohex-1-enyl)-4'-(4-ethylcyclohex-1-enyl)-biphenyl,
4-(4-n-hexylcyclohex-1-enyl)-4'-(4-ethylcyclohex-1-enyl)-biphenyl,
4-(4-n-heptylcyclohex-1-enyl)-4'-(4-ethylcyclohex-1-enyl)-biphenyl,
4-(4-n-octylcyclohex-1-enyl)-4'-(4-ethylcyclohex-1-enyl)-biphenyl,
4-(4-n-nonylcyclohex-1-enyl)-4'-(4-ethylcyclohex-1-enyl)-biphenyl,
4-(4-n-decylcyclohex-1-enyl)-4'-(4-ethylcyclohex-1-enyl)-biphenyl,
4-[4-(2-methylbutyl)-cyclohex-1-enyl]-4'-(4-ethylcyclohex-1-enyl)-biphenyl,
4-(4-n-butylcyclohex-1-enyl)-4'-(4-n-propylcyclohex-1-enyl)-biphenyl,
4-(4-n-pentylcyclohex-1-enyl)-4'-(4-n-propylcyclohex-1-enyl)-biphenyl,
4-(4-n-hexylcyclohex-1-enyl)-4'-(4-n-propylcyclohex-1-enyl)-biphenyl,
4-(4-n-heptylcyclohex-1-enyl)-4'-(4-n-propylcyclohex-1-enyl)-biphenyl.
4-(4-n-octylcyclohex-1-enyl)-4'-(4-n-propylcyclohex-1-enyl)-biphenyl,
4-(4-n-nonylcyclohex-1-enyl)-4'-(4-n-propylcyclohex-1-enyl)-biphenyl,
4-(4-n-decylcyclohex-1-enyl)-4'-(4-n-propylcyclohex-1-enyl)-biphenyl,
4-[4-(2-methylbutyl)-cyclohex-1-enyl]-4'-(4-n-propylcyclohex-1-enyl)-biphenyl,
4-(4-n-pentylcyclohex-1-enyl)-4'-(4-n-butylcyclohex-1-enyl)-biphenyl,
4-(4-n-hexylcyclohex-1-enyl)-4'-(4-n-butylcyclohex-1-enyl)-biphenyl,
4-(4-n-heptylcyclohex-1-enyl)-4'-(4-n-butylcyclohex-1-enyl)-biphenyl,
4-(4-n-octylcyclohex-1-enyl)-4'-(4-n-butylcyclohex-1-enyl)-biphenyl,
4-(4-n-nonylcyclohex-1-enyl)-4'-(4-n-butylcyclohex-1-enyl)-biphenyl,
4-(4-n-dodecylcyclohex-1-enyl)-4'-(4-n-butylcyclohex-1-enyl)-diphenyl,
4-[4-(2-methylbutyl)-cyclohex-1-enyl]-4'-(4-n-butylcyclohex-1-enyl)-biphenyl,
4-(4-n-hexylcyclohex-1-enyl)-4'-(4-n-pentylcyclohex-1-enyl)-biphenyl,
4-(4-n-heptylcyclohex-1-enyl)-4'-(4-n-pentylcyclohex-1-enyl)-biphenyl,
4-(4-n-octylcyclohex-1-enyl)-4'-(4-n-pentylcyclohex-1-enyl)-biphenyl,
4-(4-n-nonylcyclohex-1-enyl)-4'-(4-n-pentylcyclohex-1-enyl)-biphenyl,
4-(4-n-decylcyclohex-1-enyl)-4'-(4-n-pentylcyclohex-1-enyl)-biphenyl,
4-[4-(2-methylbutyl)-cyclohex-1-enyl]-4'-(4-n-pentylcyclohex-1-enyl)-biphenyl,
4-(4-n-heptylcyclohex-1-enyl)-4'-(4-n-hexylcyclohex-1-enyl)-biphenyl,
4-(4-n-octylcyclohex-1-enyl)-4'-(4-n-hexylcyclohex-1-enyl)-biphenyl,
4-(4-n-nonycyclohex-1-enyl)-4'-(4-n-hexylcyclohex-1-enyl)-biphenyl,
4-(4-n-decylcyclohex-1-enyl)-4'-(4-n-hexylcyclohex-1-enyl)-biphenyl, and
4-[4-(2-methylbutyl)-cyclohex-1-enyl]-4'-(4-n-hexylcyclohex-1-enyl)-biphenyl.

EXAMPLE 5

The following compounds of this invention are prepared in a manner analogous to that in Example 4, starting from the corresponding 4-(trans-4-alkylcyclohexyl)-bromobenzenes or 4-(trans-4-alkylcyclohexyl)-4'-bromobiphenyls:

1-(4-methylcyclohex-1-enyl)-4-(trans-4-methylcyclohexyl)-benzene,
1-(4-ethylcyclohex-1-enyl)-4-(trans-4-methylcyclohexyl)-benzene,
1-(4-n-propylcyclohex-1-enyl)-4-(trans-4-methylcyclohexyl)-benzene,
1-(4-n-butylcyclohex-1-enyl)-4-(trans-4-methylcyclohexyl)-benzene,
1-(4-n-pentylcyclohex-1-enyl)-4-(trans-4-methylcyclohexyl)-benzene,
1-(4-n-hexylcyclohex-1-enyl)-4-(trans-4-methylcyclohexyl)-benzene,
1-(4-n-heptylcyclohex-1-enyl)-4-(trans-4-methylcyclohexyl)-benzene,
1-(4-n-octylcyclohex-1-enyl)-4-(trans-4-methylcyclohexyl)-benzene,
1-(4-n-nonylcyclohex-1-enyl)-4-(trans-4-methylcyclohexyl)-benzene,
1-(4-n-decylcyclohex-1-enyl)-4-(trans-4-methylcyclohexyl)-benzene,
1-[4-(2-methylbutyl)-cyclohex-1-enyl]-4-(trans-4-methylcyclohexyl)-benzene,
1-(4-methylcyclohex-1-enyl)-4-(trans-4-ethylcyclohexyl)-benzene,
1-(4-ethylcyclohex-1-enyl)-4-(trans-4-ethylcyclohexyl)-benzene,
1-(4-n-propylcyclohex-1-enyl)-4-(trans-4-ethylcyclohexyl)-benzene,
1-(4-n-butylcyclohex-1-enyl)-4-(trans-4-ethylcyclohexyl)-benzene,
1-(4-n-pentylcyclohex-1-enyl)-4(trans-4-ethylcyclohexyl)-benzene,
1-(4-n-hexylcyclohex-1-enyl)-4-(trans-4-ethylcyclohexyl)-benzene,
1-(4-n-heptylcyclohex-1-enyl)-4-(trans-4-ethylcyclohexyl)-benzene,
1-(4-n-octylcyclohex-1-enyl)-4-(trans-4-ethylcyclohexyl)-benzene,
1-(4-n-nonylcyclohex-1-enyl)-4-(trans-4-ethylcyclohexyl)-benzene,
1-(4-n-decylcyclohex-1-enyl)-4-(trans-4-ethylcyclohexyl)-benzene,
1-[4-(2-methylbutyl)-cyclohex-1-enyl]-4-(trans-4-ethylcyclohexyl)-benzene,
1-(4-methylcyclohex-1-enyl)-4-(trans-4-n-propylcyclohexyl)-benzene,
1-(4-ethylcyclohex-1-enyl)-4-(trans-4-n-propylcyclohexyl)-benzene,
1-(4-n-propylcyclohex-1-enyl)-4-(trans-4-n-propylcyclohexyl)-benzene, 1-(4-n-butylcyclohex-1-enyl)-4-(trans-4-n-propylcyclohexyl)-benzene,
1-(4-n-pentylcyclohex-1-enyl)-4-(trans-4-n-propylcyclohexyl)-benzene,
1-(4-n-hexylcyclohex-1-enyl)-4-(trans-4-n-propylcyclohexyl)-benzene,
1-(4-n-heptylcyclohex-1-enyl)-4-(trans-4-n-propylcyclohexyl)-benzene,
1-(4-n-octylcyclohex-1-enyl)-4-(trans-4-n-propylcyclohexyl)-benzene,
1-(4-n-nonylcyclohex-1-enyl)-4-(trans-4-n-propylcyclohexyl)-benzene,
1-(4-n-decylcyclohex-1-enyl)-4-(trans-4-n-propylcyclohexyl)-benzene,
1-[4-(2-methylbutyl)-cyclohex-1-enyl]-4-(trans-4-n-propylcyclohexyl)-benzene,
1-(4-methylcyclohex-1-enyl)-4-(trans-4-n-butylcyclohexyl)-benzene,
1-(4-ethylcyclohex-1-enyl)-4-(trans-4-n-butylcyclohexyl)-benzene,
1-(4-n-propylcyclohex-1-enyl)-4-(trans-4-n-butylcyclohexyl)-benzene,
1-(4-n-butylcyclohex-1-enyl)-4-(trans-4n-butylcyclohexyl)-benzene,
1-(4-n-pentylcyclohex-1-enyl)-4-(trans-4-n-butylcyclohexyl)-benzene,
1-(4-n-hexylcyclohex-1-enyl)-4-(trans-4-n-butylcyclohexyl)-benzene,
1-(4-n-heptylcyclohex-1-enyl)-4-(trans-4-n-butylcyclohexyl)-benzene,
1-(4-n-octylcyclohex-1-enyl)-4-(trans-4-n-butylcyclohexyl)-benzene,
1-(4-n-nonylcyclohex-1-enyl)-4-(trans-4-n-butylcyclohexyl)-benzene,
1-(4-n-decylcyclohex-1-enyl)-4-(trans-4-n-butylcyclohexyl)-benzene,
1-[4-(2-methylbutyl)-cyclohex-1-enyl]-4-(trans-4-n-butylcyclohexyl)-benzene,
1-(4-methylcyclohex-1-enyl)-4-(trans-4-n-pentylcyclohexyl)-benzene,
1-(4-ethylcyclohex-1-enyl)-4-(trans-4-n-pentylcyclohexyl)-benzene,
1-(4-n-propylcyclohex-1-enyl)-4-(trans-4-n-pentylcyclohexyl)-benzene,
1-(4-n-butylcyclohex-1-enyl)-4-(trans-4-n-pentylcyclohexyl)-benzene,
1-(4-n-pentylcyclohex-1-enyl)-4-(trans-4-n-pentylcyclohexyl)-benzene,
1-(4-n-hexylcyclohex-1-enyl)-4-(trans-4-n-pentylcyclohexyl)-benzene,
1-(4-n-heptylcyclohex-1-enyl)-4-(trans-4-n-pentylcyclohexyl)-benzene,
1-(4-n-octylcyclohex-1-enyl)-4-(trans-4-n-pentylcyclohexyl)-benzene,
1-(4-n-nonylcyclohex-1-enyl)-4-(trans-4-n-pentylcyclohexyl)-benzene,
1-(4-n-decylcyclohex-1-enyl)-4-(trans-4-n-pentylcyclohexyl)-benzene,
1-[4-(2-methylbutyl)-cyclohex-1-enyl]-4-(trans-4-n-pentylcyclohexyl)-benzene,
1-(4-methylcyclohex-1-enyl)-4-(trans-4-n-hexylcyclohexyl)-benzene,
1-(4-ethylcyclohex-1-enyl)-4-(trans-4-n-hexylcyclohexyl)-benzene,
1-(4-n-propylcyclohex-1-enyl)-4-(trans-4-n-hexylcyclohexyl)-benzene,
1-(4-n-butylcyclohex-1-enyl)-4-(trans-4-n-hexylcyclohexyl)-benzene,
1-(4-n-pentylcyclohex-1-enyl)-4-(trans-4n-hexylcyclohexyl)-benzene,
1-(4-n-hexylcyclohex-1-enyl)-4-(trans-4-n-hexylcyclohexyl)-benzene,
1-(4-n-heptylcyclohex-1-enyl)-4-(trans-4-n-hexylcyclohexyl)-benzene,
1-(4-n-octylcyclohex-1-enyl)-4-(trans-4-n-hexylcyclohexyl)-benzene,
1-(4-n-nonylcyclohex-1-enyl)-4-(trans-4-n-hexylcyclohexyl)-benzene,
1-(4-n-decylcyclohex-1-enyl)-4-(trans-4-n-hexylcyclohexyl)-benzene,
1-[4-(2-methylbutyl)-cyclohex-1-enyl]-4-(trans-4-n-hexylcyclohexyl)-benzene,
1-(4-methylcyclohex-1-enyl)-4-(trans-4-n-heptylcyclohexyl)-benzene,
1-(4-ethylcyclohex-1-enyl)-4-(trans-4-n-heptylcyclohexyl)-benzene,
1-(4-n-propylcyclohex-1-enyl)-4-(trans-4-n-heptylcyclohexyl)-benzene,
1-(4-n-butylcyclohex-1-enyl)-4-(trans-4-n-heptylcyclohexyl)-benzene,
1-(4-n-pentylcyclohex-1-enyl)-4-(trans-4-n-heptylcyclohexyl)-benzene,
1-(4-n-hexylcyclohex-1-enyl)-4-(trans-4-n-heptylcyclohexyl)-benzene,
1-(4-n-heptylcyclohex-1-enyl)-4-(trans-4-n-heptylcyclohexyl)-benzene,
1-(4-n-octylcyclohex-1-enyl)-4-(trans-4-n-heptylcyclohexyl)-benzene,
1-[4-(2-methylbutyl)-cyclohex-1-enyl]-4-(trans-4-n-heptylcyclohexyl)-benzene,
1-(4-methylcyclohex-1-enyl)-4-(trans-4-n-octylcyclohexyl)-benzene,
1-(4-ethylcyclohex-1-enyl)-4-(trans-4-n-octylcyclohexyl)-benzene,
1-(4-n-propylcyclohex-1-enyl)-4-(trans-4-n-octylcyclohexyl)-benzene,
1-(4-n-butylcyclohex-1-enyl)-4-(trans-4-n-octylcyclohexyl)-benzene,
1-(4-n-pentylcyclohex-1-enyl)-4-(trans-4-n-octylcyclohexyl)-benzene,
1-(4-n-hexylcyclohex-1-enyl)-4-(trans-4-n-octylcyclohexyl)-benzene,
1-(4-n-heptylcyclohex-1-enyl)-4-(trans-4-n-octylcyclohexyl)-benzene,
1-(4-n-octylcyclohex-1-enyl)-4-(trans-4-n-octylcyclohexyl)-benzene,
1-[4-(2-methylbutyl)-cyclohex-1-enyl]-4-(trans-4-n-octylcyclohexyl)-benzene,
1-(4-methylcyclohex-1-enyl)-4-(trans-4-n-nonylcyclohexyl)-benzene,
1-(4-ethylcyclohex-1-enyl)-4-(trans-4-n-nonylcyclohexyl)-benzene,
1-(4-n-propylcyclohex-1-enyl)-4-(trans-4-n-nonylcyclohexyl)-benzene,
1-(4-n-butylcyclohex-1-enyl)-4-(trans-4-n-nonylcyclohexyl)-benzene,
1-(4n-pentylcyclohex-1-enyl)-4-(trans-4-n-nonylcyclohexyl)-benzene,
1-(4-n-hexylcyclohex-1-enyl)-4-(trans-4-n-nonylcyclohexyl)-benzene,
1-(4-methylcyclohex-1-enyl)-4-(trans-4-n-decylcyclohexyl)-benzene,
1-(4-ethylcyclohex-1-enyl)-4-(trans-4-n-decylcyclohexyl)-benzene,
1-(4-n-propylcyclohex-1-enyl)-4-(trans-4-n-decylcyclohexyl)-benzene, 1-(4-n-butylcyclohex-1-enyl)-4-(trans-4-n-decylcyclohexyl)-benzene,
1-(4-n-pentylcyclohex-1-enyl)-4-(trans-4-n-decylcyclohexyl)-benzene,
1-(4-n-hexylcyclohex-1-enyl)-4-(trans-4-n-decylcyclohexyl)-benzene,
4-(4-methylcyclohex-1-enyl)-4'-(trans-4-methylcyclohexyl)-biphenyl,
4-(4-ethylcyclohex-1-enyl)-4'-(trans-4-methylcyclohexyl)-biphenyl,
4-(4-n-propylcyclohex-1-enyl)-4'-(trans-4-methylcyclohexyl)-biphenyl,
4-(4-n-butylcyclohex-1-enyl)-4'-(trans-4-methylcyclohexyl)-biphenyl,
4-(4-n-pentylcyclohex-1-enyl)-4'-(trans-4-methylcyclohexyl)-biphenyl,
4-(4-n-hexylcyclohex-1-enyl)-4'-(trans-4-methylcyclohexyl)-biphenyl,
4-(4-n-heptylcyclohex-1-enyl)-4'-(trans-4-methylcyclohexyl)-biphenyl,
4-(4-n-octylcyclohex-1-enyl)-4'-(trans-4-methylcyclohexyl)-biphenyl,
4-(4-n-nonylcyclohex-1-enyl)-4'-(trans-4-methylcyclohexyl)-biphenyl,
4-(4-n-decylcyclohex-1-enyl)-4'-(trans-4-methylcyclohexyl)-biphenyl,
4-[4-(2-methylbutyl)-cyclohex-1-enyl]-4'-(trans-4-methylcyclohexyl-biphenyl,
4-(4-methylcyclohex-1-enyl)-4'-(trans-4-ethylcyclohexyl)-biphenyl,
4-(4-ethylcyclohex-1-enyl)-4'-(trans-4-ethylcyclohexyl)-biphenyl,
4-(4-n-propylcyclohex-1-enyl)-4'-(trans-4-ethylcyclohexyl)-biphenyl,
4-(4-n-butylcyclohex-1-enyl)-4'-(trans-4-ethylcyclohexyl)-biphenyl,
4-(4-n-pentylcyclohex-1-enyl)-4'-(trans-4-ethylcyclohexyl)-biphenyl,
4-(4-n-hexylcyclohex-1-enyl)-4'-(trans-4-ethylcyclohexyl)-biphenyl,
4-(4-n-heptylcyclohex-1-enyl)-4'-(trans-4-ethylcyclohexyl)-biphenyl,
4-(4-n-octylcyclohex-1-enyl)-4'-(trans-4-ethylcyclohexyl)-biphenyl,
4-(4-n-nonylcyclohex-1-enyl)-4'-(trans-4-ethylcyclohexyl)-biphenyl,
4-(4-n-decylcyclohex-1-enyl)-4'-(trans-4-ethylcyclohexyl)-biphenyl,
4-[4-(2-methylbutyl)-cyclohex-1-enyl]-4'-(trans-4-ethylcyclohexyl)-biphenyl,
4-(4-methylcyclohex-1-enyl)-4'-(trans-4-n-propylcyclohexyl)-biphenyl,
4-(4-ethylcyclohex-1-enyl)-4'-(trans-4-n-propylcyclohexyl)-biphenyl,
4-(4-n-propylcyclohex-1-enyl)-4'-(trans-4-n-propylcyclohexyl)-biphenyl,
4-(4-n-butylcyclohex-1-enyl)-4'-(trans-4-n-propylcyclohexyl)-biphenyl,
4-(4-n-pentylcyclohex-1-enyl)-4'-(trans-4-n-propylcyclohexyl)-biphenyl,
4-(4-n-hexylcyclohex-1-enyl)-4'-(trans-4-n-propylcyclohexyl)-biphenyl,
4-(4-n-heptylcyclohex-1-enyl)-4'-(trans-4-n-propylcyclohexyl)-biphenyl,
4-(4-n-octylcyclohex-1-enyl)-4'-(trans-4-n-propylcyclohexyl)-biphenyl,
4-(4-n-nonylcyclohex-1-enyl)-4'-(trans-4-n-propylcyclohexyl)-biphenyl,
4-(4-n-decylcyclohex-1-enyl)-4'-(trans-4-n-propylcyclohexyl)-biphenyl,
4-[4-(2-methylbutyl)-cyclohex-1-enyl]-4'-(trans-4-n-propylcyclohexyl)-biphenyl,
4-(4-methylcyclohex-1-enyl)-4'-(trans-4-n-butylcyclohexyl)-biphenyl,
4-(4-ethylcyclohex-1-enyl)-4'-(trans-4-n-butylcyclohexyl)-biphenyl,
4-(4-n-propylcyclohex-1-enyl)-4'-(trans-4-n-butylcyclohexyl)-biphenyl,
4-(4-n-butylcyclohex-1-enyl)-4'-(trans-4-n-butylcyclohexyl)-biphenyl,
4-(4-n-pentylcyclohex-1-enyl)-4'-(trans-4-n-butylcyclohexyl)-biphenyl,
4-(4-n-hexylcyclohex-1-enyl)-4'-(trans-4-n-butylcyclohexyl)-biphenyl,
4-(4-n-heptylcyclohex-1-enyl)-4'-(trans-4-n-butylcyclohexyl)-biphenyl,
4-(4n-octylcyclohex-1-enyl)-4'-(trans-4-n-butylcyclohexyl)-biphenyl,
4-(4-n-nonylcyclohex-1-enyl)-4'-(trans-4-n-butylcyclohexyl)-biphenyl,
4-(4-n-decylcyclohex-1-enyl)-4'-(trans-4-n-butylcyclohexyl)-biphenyl,
4-[4-(3-methylbutyl)-cyclohex-1-enyl]-4'-(trans-4-n-butylcyclohexyl)-biphenyl,
4-(4-methylcyclohex-1-enyl)-4'-(trans-4-n-pentylcyclohexyl)-biphenyl,
4-(4-ethylcyclohex-1-enyl)-4'-(trans-4-n-pentylcyclohexyl)-biphenyl,
4-(4-n-propylcyclohex-1-enyl)-4'-(trans-4-n-pentylcyclohexyl)-biphenyl,
4-(4-n-butylcyclohex-1-enyl)-4'-(trans-4-n-pentylcyclohexyl)-biphenyl,
4-(4-n-pentylcyclohex-1-enyl)-4'-(trans-4-n-pentylcyclohexyl)-biphenyl,
4-(4-n-hexylcyclohex-1-enyl)-4'-(trans-4-n-pentylcyclohexyl)-biphenyl,
4-(4-n-heptylcyclohex-1-enyl)-4'-(trans-4-n-pentylcyclohexyl)-biphenyl,
4-(4-n-octylcyclohex-1-enyl)-4'-(trans-4-n-pentylcyclohexyl)-biphenyl,
4-(4-n-nonylcyclohex-1-enyl)-4'-(trans-4-n-pentylcyclohexyl)-biphenyl,
4-[4-(2-methylbutyl)-cyclohex-1-enyl]-4'-(trans-4-n-pentylcyclohexyl)-biphenyl,
4-(4-methylcyclohex-1-enyl)-4'-(trans-4-n-hexylcyclohexyl)-biphenyl,
4-(4-ethylcyclohex-1-enyl)-4'-(trans-4-n-hexylcyclohexyl)-biphenyl,
4-(4-n-propylcyclohex-1-enyl)-4'-(trans-4-n-hexylcyclohexyl)-biphenyl,
4-(4-n-butylcyclohex-1-enyl)-4'-(trans-4-n-hexylcyclohexyl)-biphenyl,
4-(4-n-pentylcyclohex-1-enyl)-4'-(trans-4-n-hexylcyclohexyl)-biphenyl,
4-(4-n-hexylcyclohex-1-enyl)-4'-(trans-4-n-hexylcyclohexyl)-biphenyl,
4-(4-n-heptylcyclohex-1-enyl)-4'-(trans-4-n-hexylcyclohexyl)-biphenyl,
4-(4-n-octylcyclohex-1-enyl)-4'-(trans-4-n-hexylcyclohexyl)-biphenyl,
4-(4-n-nonylcyclohex-1-enyl)-4'-(trans-4-n-hexylcyclohexyl)-biphenyl,
4-(4-n-decylcyclohex-1-enyl)-4'-(trans-4-n-hexylcyclohexyl)-biphenyl,
4-[4-(2-methylbutyl)-cyclohex-1-enyl]-4'-(trans-4-n-hexylcyclohexyl)-biphenyl, 4-(4-methylcyclohex-1-enyl)-4'-(trans-4-n-heptylcyclohexyl)-biphenyl,
4-(4-ethylcyclohex-1-enyl)-4'-(trans-4-n-heptylcyclohexyl)-biphenyl,
4-(4-n-propylcyclohex-1-enyl)-4'-(trans-4-n-heptylcyclohexyl)-biphenyl,
4-(4-n-butylcyclohex-1-enyl)-4'-(trans-4-n-heptylcyclohexyl)-biphenyl,
4-(4-n-pentylcyclohex-1-enyl)-4'-(trans-4-n-heptylcyclohexyl)-biphenyl,
4-(4-n-hexylcyclohex-1-enyl)-4'-(trans-4-n-heptylcyclohexyl)-biphenyl,
4-(4-n-heptylcyclohex-1-enyl)-4'-(trans-4-n-heptylcyclohexyl)-biphenyl,
4-[4-(2-methylbutyl)-cyclohex-1-enyl]-4'-(trans-4-n-heptylcyclohexyl)-benzene,
4-(4-methylcyclohex-1-enyl)-4'-(trans-4-n-octylcyclohexyl)-biphenyl,
4-(4-ethylcyclohex-1-enyl)-4'-(trans-4-n-octylcyclohexyl)-biphenyl,
4-(4-n-propylcyclohex-1-enyl)-4'-(trans-4-n-octylcyclohexyl)-biphenyl,
4-(4-n-butylcyclohex-1-enyl)-4'-(trans-4-n-octylcyclohexyl)-biphenyl,
4-(4-n-pentylcyclohex-1-enyl)-4'-(trans-4-n-octylcyclohexyl)-biphenyl,
4-(4-n-hexylcyclohex-1-enyl)-4'-(trans-4-n-octylcyclohexyl)-biphenyl,
4-[4-(2-methylbutyl)-cyclohex-1-enyl]-4'-(trans-4-n-octylcyclohexyl)-benzene,
4-(4-methylcyclohex-1-enyl)-4'-(trans-4-n-nonylcyclohexyl)-biphenyl.
4-(4-ethylcyclohex-1-enyl)-4'-(trans-4-n-nonylcyclohexyl)-biphenyl,
4-(4-n-propylcyclohex-1-enyl)-4'-(trans-4-n-nonylcyclohexyl)-biphenyl,
4-(4-n-butylcyclohex-1-enyl)-4'-(trans-4-n-nonylcyclohexyl)-biphenyl,
4-(4-n-pentylcyclohex-1-enyl)-4'-(trans-4-n-nonylcyclohexyl)-biphenyl.
4-(4-n-hexylcyclohex-1-enyl)-4'-(trans-4-n-nonylcyclohexyl)-biphenyl,
4-(4-methylcyclohex-1-enyl)-4'-(trans-4-n-decylcyclohexyl)-biphenyl,
4-(4-ethylcyclohex-1-enyl)-4'-(trans-4-n-decylcyclohexyl)-biphenyl,
4-(4-n-propylcyclohex-1-enyl)-4'-(trans-4-n-decylcyclohexyl)-biphenyl,
4-(4-n-butylcyclohex-1-enyl)-4'-(trans-4-n-decylcyclohexyl)-biphenyl,
4-(4-n-pentylcyclohex-1-enyl)-4'-(trans-4-n-decylcyclohexyl)-biphenyl and
4-(4-n-hexylcyclohex-1-enyl)-4'-(trans-4-n-decylcyclohexyl)-biphenyl.

The following examples relate to the use of the partially hydrogenated oligo-1,4-phenylenes of this invention as components of liquid crystal dielectrics.

Example 6

(a) A dielectric consisting of 33.3% of 4-n-butyl-4'-methoxyazoxybenzene, 16.7% of 4-ethyl-4'-methoxyazoxy-benzene and 50.0% of 4-(trans-4-n-pentylcyclohexyl)-benzonitrile has a clear point of 64°, a threshold voltage in a twisted nematic cell of 1.7 V at 40° and a temperature dependence of the threshold voltage of 10.5 mV per degree Centigrade.

(b) In contrast, a dielectric of 86% of the mixture described above and 14% of the compound 4-(trans-4-n-pentylcyclohexyl)-4'-(trans-4-n-hexylcyclohexyl)-biphenyl of this invention has a clear point of 80°, a threshold voltage in a twisted nematic cell of 1.9 V at 40° and a temperature dependence of the threshold voltage of only 4.7 mV per degree Centigrade.

Example 7

(a) A dielectric consisting of 12% of 4-(trans-4-ethylcyclohexyl)-benzonitrile, 23% of 4-(trans-4n-butylcyclohexyl)-benzonitrile, 14% of 4-ethyl-4'-cyanobiphenyl, 10% of 4-n-propyloxy-4'-cyanobiphenyl, 20% of 4-(trans-4-ethylcyclohexyl)benzoic acid (trans-4-propylcyclohexyl) ester and 21% of 4-(trans-4-butylcyclohexyl)benzoic acid (trans-4-n-propylcyclohexyl) ester has a m. of −5°, a c. of 68°, a threshold voltage in a twisted nematic cell of 1.52 V at 40° and a temperature dependence of the threshold voltage of 6.0 mV per degree Centigrade.

(b) In contrast, a dielectric consisting of 90% of the mixture described above and 10% of the compound 4-(trans-4-n-pentylcyclohexyl)-4'-(trans-4-n-hexylcyclohexyl)-biphenyl of this invention has a m. of −6°, a c. of 81°, a threshold voltage in a twisted nematic cell of 1.74 V at 40° and a temperature dependence of the threshold voltage of only 3.0 mV per degree Centigrade.

Example 8

(a) A dielectric consisting of 24% of 4-(trans-4-n-propylcyclohexyl)-benzonitrile, 36% of 4-(trans-4-n-pentylcyclohexyl)-benzonitrile, 25% of 4-(trans-4-n-heptylcyclohexyl)-benzonitrile and 15% of 4-(trans-4-n-pentylcyclohexyl)-4'-cyanobiphenyl has a m. of −6°, a c. of 72°, a threshold voltage in a twisted nematic cell of 1.7 V at 40° and a temperature dependence of the threshold voltage of 10.0 mV per degree Centigrade.

(b) In contrast, a dielectric consisting of 90% of the mixture described above and 10% of the compound 4,4-bis(trans-4-n-pentylcyclohexyl)-biphenyl of this invention has a m. of −7°, a c. of 88°, a threshold voltage in a twisted nematic cell of 2.0 V at 40° and a temperature dependence of the threshold voltage of only 7.5 mV per degree Centigrade.

Example 9

A dielectric consisting of
28% of 4-n-pentylphenyl anisate,
22% of 4-n-propylphenyl 4-n-hexanoyloxybenzoate
20% of 4-n-propylcyclohexyl 4-(trans-4-n-butylcyclohexyl)-benzoate
19% of 4-(trans-4-n-propylcyclohexyl)-ethylbenzene and
11% of 4-(trans-4-n-pentylcyclohexyl) 4'-(trans-4-n-propylcyclohexyl) biphenyl
has a nematic mesophase in the temperature range of from −7° to +70°, a viscosity of $35 \cdot 10^{-3}$ Pa.s at 20° and a dielectric anisotropy of −0.2. It is particularly useful for liquid crystal displays using the phenomenon of dynamic scattering.

Example 10

A dielectric consisting of
23% of 4-(trans-4-n-pentylcyclohexyl) benzonitrile,
17% of 4-(trans-4-n-propylcyclohexyl) benzonitrile,
16% of 4-(trans-4-n-propylcyclohexyl) phenetole,
12% of 4-(trans-4-n-propylcyclohexyl) 1-n-butyloxybenzene, 22% of 4-(trans-4-n-pentylcyclohexyl) 4'-ethyl biphenyl, and 10% of 4-(trans-4-n-pentylcyclohexyl) 4'-(trans-4-n-propylcyclohexyl) biphenyl has a nematic mesophase in the temperature range of from −20° to +85, a viscosity of 19·10⁻³ Pa.s at 20°, a dielectric anisotropy of +6, a threshold voltage in a twisted nematic cell of 2.3 V at 20°, and a temperature dependence of the threshold voltage of only 8 mV per degree Centigrade. The particularly low viscosity and the broad temperature range of the nematic mesophase make this dielectric particularly useful for liquid crystal displays for the use in motor vehicles.

Example 11

A dielectric consisting of

49% of 4-(trans-4-n-propylcyclohexyl) 1-n-butyryloxybenzene,

21% of 4-(trans-4-n-propylcyclohexyl) phenetole,

18% of 4-(trans-4-n-propylcyclohexyl) 1-n-butyloxy benzene, and

12% of 4-(trans-4-n-propylcyclohexyl) 4'-(trans-4-n-pentylcyclohexyl) biphenyl has a nematic mesophase in the temperature range of from −10° to +59°, a viscosity of 13·10⁻³ Pa.s at 20° C. only, and a dielectric anisotropy of −0.59. It is especially well suited for dynamic scattering liquid crystal displays operated at rather low voltage.

Example 12

A dielectric consisting of

21% of 4-(trans-4-n-pentylcyclohexyl) benzonitrile,

14% of 4-(trans-4-n-propylcyclohexyl) benzonitrile,

16% of 4-(trans-4-n-propylcyclohexyl) phenetole,

12% of 4-(trans-4-n-propylcyclohexyl) 1-n-butyloxybenzene,

22% of 4-(trans-4-n-pentylcyclohexyl) 4'-ethyl biphenyl,

5% of 4-(trans-4-n-pentylcyclohexyl) 4'-cyano biphenyl, and

10% of 4-(trans-4-n-pentylcyclohexyl) 4'-(trans-4-n-propylcyclohexyl) biphenyl has a nematic mesophase in the temperature range of from −20° to +90°, a viscosity of 22·10⁻³ Pa.s at 20°, a dielectric anisotropy of +5.7 and a threshold voltage of 2.3 V in a twisted nematic cell. This dielectric is especially useful for motor vehicle dashboard displays.

Example 13

A dielectric consisting of

20% of 4-(trans-4-n-butylcyclohexyl) benzonitrile,

18% of 4-(trans-4-n-pentylcyclohexyl) benzonitrile,

17% of 4-n-butyl 4'-cyanobiphenyl,

13% of 4-ethyl 4'-cyanobiphenyl,

12% of 4-n-propylphenyl 4-(trans-4-n-propylcyclohexyl) benzoate,

10% of 4-(trans-4-n-pentylcyclohexyl) 4'-ethyl biphenyl, and

10% of 4-(trans-4-n-pentylcyclohexyl) 4'-(trans-4-n-propylcyclohexyl) biphenyl has a nematic mesophase in the temperature range of from −4° to +84°, a viscosity of 30·10⁻³ Pa.s at 20°, a dielectric anisotropy of +10, a threshold voltage of 1.5 V at 20° in a twisted nematic cell, and a temperature dependence of the threshold voltage of 4 mV per degree Centigrade only. This dielectric is most useful for high information systems based on matrix addressed twisted nematic cells.

Example 14

A dielectric consisting of

20% of 4-(trans-4-n-propylcyclohexyl) benzonitrile,

16% of 4-(trans-4-n-butylcyclohexyl) benzonitrile,

22% of 4-(trans-4-n-pentylcyclohexyl) benzonitrile,

25% of 4-(trans-4-n-pentylcyclohexyl) 4'-ethyl biphenyl,

7% of 4-(trans-4-n-propylcyclohexyl) ethylbenzene, and

10% of 4-(trans-4-n-pentylcyclohexyl) 4'-(trans-4-n-propylcyclohexyl) biphenyl has a nematic mesophase in the temperature range of from −15° to +85°, a viscosity of 21·10⁻³ Pa.s. at 20°, a dielectric anisotropy of +7.5, a threshold voltage of 1.8 V at 20° in a twisted nematic cell, and a temperature dependence of the threshold voltage of 7 mV per degree centigrade.

Example 15

A dielectric consisting of

16% of 4-(trans-4-ethylcyclohexyl) benzonitrile,

22% of 4-(trans-4-n-propylcyclohexyl) benzonitrile,

17% of 4-(trans-4-n-butylcyclohexyl) benzonitrile,

27% of 4-(trans-4-n-pentylcyclohexyl) benzonitrile,

8% of 4-(trans-4-n-pentylcyclohexyl) 4'-ethyl biphenyl, and

10% of 4-(trans--4-n-pentylcyclohexyl) 4'-(trans-4-n-propylcyclohexyl) biphenyl has a nematic mesophase in the temperature range of from −10° to +66°, a viscosity of 23·10⁻³ Pa.s at 20° and a dielectric anisotropy of +9.7. The threshold voltage in a twisted nematic cell is 1.6 V. Displays comprising this dielectric can advantageously be used, e.g., in portable calculators.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

We claim:

1. A partially hydrogenated oligo-1,4-phenylene of the formula

wherein n is 1 or 2, the rings A and B are identical or different and are trans-4-alkylcyclohexyl or 4-alkylcyclohex-1-enyl, and the alkyl groups in each case are of up to 10 carbon atoms, and are straight chained or branched containing only one chain branching.

2. A partially hydrogenated oligo-1,4-phenylene of claim 1 of the formula

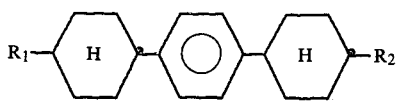

wherein $R_1$ and $R_2$ are identical or different and are alkyl of up to 10 carbon atoms.

3. A partially hydrogenated oligo-1,4-phenylene of claim 1 of the formula

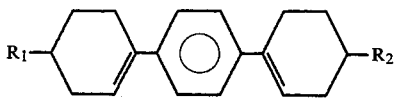

wherein $R_1$ and $R_2$ are identical or different and are alkyl of up to 10 carbon atoms.

4. A partially hydrogenated oligo-1,4-phenylene of claim 1 of the formula

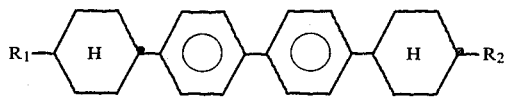

wherein $R_1$ and $R_2$ are identical or different and are alkyl of up to 10 carbon atoms.

5. A partially hydrogenated oligo-1,4-phenylene of claim 1 of the formula

wherein $R_1$ and $R_2$ are identical or different and are alkyl of up to 10 carbon atoms.

6. A compound of claim 1 wherein the alkyl groups on the A and B rings together contain 4–13 carbon atoms.

7. A liquid crystal dielectric comprising two liquid crystalline components at least one of which is a compound of claim 1.

8. An electro-optical display element comprising an electro-optical liquid crystal cell containing a liquid crystal dielectric of claim 7.

9. A partially hydrogenated oligo-1,4-phenylene of claim 1 wherein at least one of the rings A or B is 4-alkylcyclohex-1-enyl.

* * * * *